(12) United States Patent
Kanatani et al.

(10) Patent No.: US 8,629,180 B2
(45) Date of Patent: Jan. 14, 2014

(54) ANTISEPTIC AGENT COMPOSITION

(75) Inventors: Shuji Kanatani, Osaka (JP); Soota Iwamoto, Osaka (JP)

(73) Assignee: Taiyo Corporation, Osaka (JP)

( * ) Notice: Subject to any disclaimer, the term of this patent is extended or adjusted under 35 U.S.C. 154(b) by 52 days.

(21) Appl. No.: 13/318,460

(22) PCT Filed: Jan. 18, 2010

(86) PCT No.: PCT/JP2010/050500
§ 371 (c)(1),
(2), (4) Date: Nov. 1, 2011

(87) PCT Pub. No.: WO2010/137354
PCT Pub. Date: Dec. 2, 2010

(65) Prior Publication Data
US 2012/0053133 A1 Mar. 1, 2012

(30) Foreign Application Priority Data

May 27, 2009 (JP) .................. 2009-127390
Aug. 19, 2009 (JP) .................. 2009-189915

(51) Int. Cl.
*A01N 37/14* (2006.01)
*A01N 31/02* (2006.01)

(52) U.S. Cl.
USPC ............ 514/549; 514/552; 514/738; 424/405

(58) Field of Classification Search
USPC .................... 514/549, 552; 424/405
See application file for complete search history.

(56) References Cited

U.S. PATENT DOCUMENTS

| 6,579,516 B1 * | 6/2003 | Mansouri ............... 424/70.1 |
| 2004/0102358 A1 * | 5/2004 | Scivoletto ............... 514/1 |
| 2005/0106191 A1 * | 5/2005 | Kobayashi et al. ......... 424/401 |
| 2010/0221197 A1 * | 9/2010 | Tanaka et al. ............ 424/49 |

FOREIGN PATENT DOCUMENTS

| JP | Hei 11-322591 | 11/1999 |
| JP | 2001-226205 | 8/2001 |
| JP | 2003-81761 | 3/2003 |
| JP | 2007-504826 | 3/2007 |
| WO | 2007/070795 | 6/2007 |
| WO | 2009/069352 | 6/2009 |

OTHER PUBLICATIONS

White et al., Antimicrob. Agents Chemother., 1996, 40(8), p. 1914-1918.*
International Search Report for PCT/JP2010/050500.
Written Opinion of the International Searching Authority for PCT/JP2010/050500.
International Preliminary Report on Patentability for PCT/JP2010/050500.
The Chemical Daily News (online), Jul. 9, 2008.
Japan Food Science, vol. 21, No. 4, 1982.
"Subject-Book of Antibacterial and Antifungal Agents" issued on Aug. 22, 1986.

* cited by examiner

*Primary Examiner* — Shaojia Anna Jiang
*Assistant Examiner* — Jonathan S Lau
(74) *Attorney, Agent, or Firm* — Vedder Price P.C.

(57) ABSTRACT

A novel antiseptic agent composition which has a wide antimicrobial spectrum and excellent antiseptic properties is provided. An antiseptic agent composition A contains a glycerin hydroxy fatty acid monoester that is an ester of glycerin and a hydroxy fatty acid having 8 to 18 carbon atoms, and a specific antiseptic agent such as an alkanediol. An antiseptic agent composition B contains the glycerin hydroxy fatty acid monoester and an aromatic antiseptic agent. An antiseptic agent composition C contains the glycerin hydroxy fatty acid monoester and a chelating agent.

2 Claims, No Drawings

US 8,629,180 B2

ANTISEPTIC AGENT COMPOSITION

BACKGROUND OF THE INVENTION

1. Field of the Invention

The present invention relates to an antiseptic agent composition, and more particularly relates to an antiseptic agent composition containing a glycerin hydroxy fatty acid monoester and a specific antiseptic agent, an aromatic antiseptic agent or a chelating agent.

2. Description of the Related Art

In order to acquire antiseptic properties and enhance preservative quality, cosmetics and medicines contain antiseptic agents. Typical examples of antiseptic agents contained in cosmetics and medicines include a p-hydroxybenzoate ester (commonly referred to as parabens). In recent years, skin irritation of parabens has become problematic, and it is desired to reduce the amount of parabens contained therein in terms of safety.

To overcome this problem, as a technology for reducing or excluding antiseptic and bactericidal agents, such as parabens, benzoic acids and salicylic acids, which are used as antiseptic and bactericidal agents for cosmetics, for example, an antiseptic and bactericidal agent composed of 1,2-alkanediol or the like is disclosed (see Patent Document 1). However, when 1,2-alkanediol such as 1,2-octanediol is used as an antiseptic and bactericidal agent, a large amount of antiseptic and bactericidal agent needs to be contained to perform prevention on a wide range of microorganisms, and its effect is not completely exerted on all species of microorganisms. Hence, it is desired to develop an antiseptic and bactericidal agent that has sufficient antiseptic and bactericidal effects.

In addition, a glycerin medium chain fatty acid ester, which is conventionally known as an antimicrobial agent of food (see Patent Document 2), has the same problems as those of 1,2-alkanediol described above.

Patent Document 1: Japanese Published Unexamined Patent Application No. H11-322591
Patent Document 2: Japanese Published Unexamined Patent Application No. 2001-226205

Under such conditions, the present applicant has found that a glycerin ricinoleic acid monoester exerts antiseptic and bactericidal effects on *S. aureus* and many other microorganisms. However, said compound exerts almost no antiseptic and bactericidal effect on *E. coli*.

SUMMARY OF THE INVENTION

The present invention is made in view of the foregoing situation; a main object of the present invention is to provide a new antiseptic agent composition that has a wide antimicrobial spectrum and excellent antiseptic properties.

As a result of intensively conducting studies to achieve the above object, the present inventors focused on a glycerin hydroxy fatty acid monoester that is an ester of glycerin and a hydroxy fatty acid having 8 to 18 carbon atoms, found that the above object could be achieved by using an antiseptic agent composition A containing the said compound and a specific antiseptic agent such as an alkanediol, an antiseptic agent composition B containing the said compound and an aromatic antiseptic agent, or an antiseptic agent composition C containing the said compound and a chelating agent, and thus completed the present invention.

The summary of the present invention is as follows.

[1] An antiseptic agent composition including: a glycerin hydroxy fatty acid monoester that is an ester of glycerin and a hydroxy fatty acid having 8 to 18 carbon atoms; and an antiseptic agent that is selected from a group consisting of an alkanediol, a sorbitan fatty acid ester, a sucrose fatty acid ester, a propylene glycol fatty acid ester, a glycerin medium chain fatty acid ester, a polyglycerin fatty acid ester, a polyoxyethylene fatty acid ester, a glycerin fatty acid ether and a polyoxyethylene alkyl ether.

[2] The antiseptic agent composition of [1] described above, in which the alkanediol is 1,2-alkanediol having 5 to 10 carbon atoms.

[3] The antiseptic agent composition of [1] described above, in which the glycerin medium chain fatty acid ester is a glycerin medium chain fatty acid monoester that is an ester of glycerin and a medium chain fatty acid having 8 to 12 carbon atoms.

[4] The antiseptic agent composition of any one of [1] to [3] described above, in which the glycerin hydroxy fatty acid monoester is a glycerin ricinoleic acid monoester.

[5] The antiseptic agent composition of [4] described above, in which the 1,2-alkanediol having 5 to 10 carbon atoms is 1,2-octanediol.

[6] The antiseptic agent composition of [4] described above, in which the glycerin medium chain fatty acid monoester is a glycerin caprylic acid monoester.

[7] An antiseptic agent composition including: a glycerin hydroxy fatty acid monoester that is an ester of glycerin and a hydroxy fatty acid having 8 to 18 carbon atoms; and an aromatic antiseptic agent.

[8] The antiseptic agent composition of [7] described above, in which the aromatic antiseptic agent is selected from a group consisting of a p-hydroxybenzoate ester, phenoxyethanol, isopropyl methylphenol, benzoic acid, benzoate, and salicylic acid.

[9] The antiseptic agent composition of [7] or [8] described above, in which the glycerin hydroxy fatty acid monoester is a glycerin ricinoleic acid monoester.

[10] An antiseptic agent composition including: a glycerin hydroxy fatty acid monoester that is an ester of glycerin and a hydroxy fatty acid having 8 to 18 carbon atoms; and a chelating agent.

[11] The antiseptic agent composition of [10] described above, in which the chelating agent is an aminocarboxylic acid chelating agent that is selected from a group consisting of ethylenediaminetetraacetic acid, hydroxyethylethylenediaminetriacetic acid, dihydroxyethylethylenediaminediacetic acid, 1,3-propanediaminetetraacetic acid, diethylenetriaminepentaacetic acid, triethylenetetraminehexaacetic acid, nitrilotriacetic acid, hydroxyethyliminodiacetic acid, L-aspartic acid-N,N-diacetic acid, amino trimethylene phosphonic acid, hydroxyethane-diphosphonic acid, and salts thereof.

[12] The antiseptic agent composition of [10] or [11] described above, in which the glycerin hydroxy fatty acid monoester is a glycerin ricinoleic acid monoester.

[13] A method of compounding the antiseptic agent composition of any one of [1] to [12] described above with an item to be antisepticized that is selected from food products, tableware, perfume cosmetics, cosmetics, external preparations for skin, oral hygiene products, quasi drugs, daily hygiene products, clothing, paints, and pet hygiene products so as to enhance an antiseptic property of the item to be antisepticized.

The antiseptic agent composition A of the present invention contains a glycerin hydroxy fatty acid monoester and a specific antiseptic agent. Thus, the antiseptic agent composition has an excellent antiseptic property against gram-positive bacteria, gram-negative bacteria and yeast, and further has significant effects (synergistic effects) of the antiseptic property against, for example, gram-negative bacteria and yeast as compared with the total effects of the antiseptic properties of individual components.

The antiseptic agent composition B of the present invention contains a glycerin hydroxy fatty acid monoester and an aromatic antiseptic agent. Thus, the antiseptic agent composition has an excellent antiseptic property against gram-positive bacteria, gram-negative bacteria and yeast, and further has significant effects (synergistic effects) of the antiseptic property against, for example, gram-negative bacteria and yeast as compared with the total effects of the antiseptic properties of individual components. Thus, it is possible to reduce the amount of aromatic antiseptic agent used and therefore increase the safety of the antiseptic agent composition.

The antiseptic agent composition C of the present invention contains a glycerin hydroxy fatty acid monoester and a chelating agent. Thus, the antiseptic agent composition has an excellent antiseptic property against gram-positive bacteria, gram-negative bacteria, yeast and mold, and further has significant effects (synergistic effects) of the antiseptic property against fungi such as yeast and mold as compared with the total effects of the antiseptic properties of individual components. Thus, it is unnecessary to compound a conventional aromatic antiseptic agent, and it is therefore possible to increase the safety of the antiseptic agent composition.

When any one of the antiseptic agent compositions A to C described above is compounded into an item to be antisepticized that is selected from, for example, food products, tableware, perfume cosmetics, cosmetics, external preparations for skin, oral hygiene products, quasi drugs, daily hygiene products, clothing, paints, and pet hygiene products, the resulting compound prevents bacterial infection and food poisoning and can be effectively applied to various cases.

DETAILED DESCRIPTION OF THE PREFERRED EMBODIMENTS

Antiseptic agent compositions of the present invention will be specifically described below in the order of A, B and C.

[Antiseptic Agent Composition A]

As described above, the antiseptic agent composition A of the present invention is characterized in that the antiseptic agent composition A contains a glycerin hydroxy fatty acid monoester and a specific antiseptic agent.

The glycerin hydroxy fatty acid monoester refers to a compound that is obtained by binding one molecule of glycerin to one molecule of hydroxy fatty acid having 8 to 18 carbon atoms through an ester bond. Examples of the fatty acid of the said glycerin hydroxy fatty acid monoester include: a ricinoleic acid; a 12-hydroxystearic acid; 10-hydroxyundecanoic acid; 9-hydroxyundecanoic acid; 8-hydroxyundecanoic acid; 5-hydroxydodecanoic acid; 5-hydroxyundecanoic acid; 5-hydroxydecanoic acid; 4-hydroxydodecanoic acid; 4-hydroxyundecanoic acid; 4-hydroxydecanoic acid; 9-hydroxy-2-decenoic acid; and 5-hydroxy-7-decenoic acid. Among them, a glycerin ricinoleic acid monoester is preferable in that its antiseptic property is particularly excellent.

The specific antiseptic agent refers to an agent that has an antiseptic property by itself and that has an enhanced antiseptic property in that, when the antiseptic agent together with the glycerin hydroxy fatty acid monoester described above is contained in an item to be antisepticized described later, as compared with a case where each of the above two compounds is individually used, the decrease in the remaining number of at least one species of bacteria is accelerated (in other words, an agent that produces a synergistic effect of an antiseptic property against at least one species of bacteria). Such an antiseptic agent can be selected from, for example, an alkanediol, a sorbitan fatty acid ester, a sucrose fatty acid ester, a propylene glycol fatty acid ester, a glycerin medium chain fatty acid ester, a polyglycerin fatty acid ester, a polyoxyethylene fatty acid ester, a glycerin fatty acid ether and a polyoxyethylene alkyl ether; one of these compounds or a mixture of two or more of the same can be used.

As the alkanediol, 1,2-alkanediol having 5 to 10 carbon atoms is preferable; examples of the alkanediol include 1,2-pentanediol, 1,2-hexanediol, 1,2-octanediol, and 1,2-decanediol. Among the above compounds, 1,2-octanediol is particularly preferable in that its antiseptic property is particularly excellent.

The sorbitan fatty acid ester, the sucrose fatty acid ester, the propylene glycol fatty acid ester, the polyglycerin fatty acid ester, and the polyoxyethylene fatty acid ester (hereinafter collectively referred to as "various fatty acid esters") are esters obtained by binding each of sorbitan, sucrose, propylene glycol, polyglycerin, and polyoxyethylene to a fatty acid though an ester bond. The constituent fatty acid is not particularly limited; a fatty acid having 8 to 20 carbon atoms is generally used. Examples of the fatty acid include caprylic acid, capric acid, lauric acid, myristic acid, palmitic acid, stearic acid, oleic acid and linoleic acid. Among the above various fatty acid esters, the polyglycerin fatty acid ester includes a monoester, a diester, and a triester; any one of these esters may be used in the present invention.

The glycerin fatty acid ether includes a monoether, a diether, and a triether; any one of these ethers may be used in the present invention. Examples of them include a glycerin mono myristyl ether, a glycerin mono stearyl ether, a glycerin mono isostearyl ether and a glycerin mono oleyl ether. Examples of the polyoxyethylene alkyl ether include a polyoxyethylene lauryl ether, a polyoxyethylene cetyl ether, a polyoxyethylene stearyl ether, and a polyoxyethylene oleyl ether.

The glycerin medium chain fatty acid ester is an ester obtained from glycerin and a medium chain fatty acid; as the constituent fatty acid, a fatty acid having 8 to 12 carbon atoms is generally used. Examples of the fatty acid include caprylic acid, capric acid, lauric acid. The glycerin medium chain fatty acid ester includes a monoester, a diester, and a triester; in terms of the antiseptic property, a monoester itself or a mixture having a high content of monoester is preferably used. Among them, in terms of the antiseptic property, a glycerin caprylic acid monoester is particularly preferable.

The antiseptic agent composition A of the present invention contains the glycerin hydroxy fatty acid monoester and the specific antiseptic agent described above. When the antiseptic agent composition of the present invention is applied to an item to be antisepticized that can be selected from, for example, food products, tableware, perfume cosmetics, cosmetics, external preparations for skin, oral hygiene products, quasi drugs, daily hygiene products, clothing, paints, and pet hygiene products, the antiseptic agent composition exerts an excellent antiseptic property against gram-positive bacteria, gram-negative bacteria, and yeast, and further has significant effects (synergistic effects) of the antiseptic property against, for example, gram-negative bacteria and yeast as compared with the total effects of the antiseptic properties of individual components.

The antiseptic agent composition A of the present invention can be widely applied to cosmetics, drugs, quasi drugs and the like that are externally applied, and can be in various forms, such as a water solution form, a soluble form, an emulsion form, an oil form, a gel form, a paste form, an ointment form, or an aerosol form. With respect to basic skin cosmetics, the antiseptic agent composition A in various forms described above can be widely applied to face washes, lotions, milky lotions, creams, gels, essences (beauty essences), packs and masks, and the like. Furthermore, with respect to makeup cosmetics, the antiseptic agent composition A in various forms described above can be widely applied to foundations, mascara, nail enamel, lipsticks and the like. Moreover, with respect to hair care cosmetics, the antiseptic agent composition A in various forms described above can be widely applied to shampoos, rinses, hair growth drugs, and the like. With respect to drugs and quasi drugs, the antiseptic agent composition A can be widely applied to various types of ointments and the like. With respect to oral hygiene products, the antiseptic agent composition A can be applied to mouthwashes, toothpastes, mouth fresheners, tablet candies, sheet-shaped films, and the like. The forms and applications of the antiseptic agent composition A according to the present invention are not limited to those forms and applications described above.

The antiseptic agent composition A of the present invention may consist only of the above glycerin hydroxy fatty acid monoester and the specific antiseptic agent; the antiseptic agent composition A can widely contain commonly known base components according to those forms and applications described above in the range in which the intended effects of the present invention are not ruined by containing the base components. Examples of other components that can be contained include purified water, ethanol, glycerin, propylene glycol, 1,3-butylene glycol, polyethylene glycol, alcohols having linear-chain and branched-chain alkyls or alkenyls, liquid paraffins, vaseline, lanolin, dimethyl polysiloxane, higher alcohol higher fatty acid esters, higher fatty acids, animal and vegetable oils and fats, synthetic ester oils, silicones, various surface acting agents, sequestering agents (chelating agents), water-soluble polymers, thickening agents, various powder components, color agents, perfumes, antioxidizing agents, ultraviolet absorbing agents and montmorillonite. Furthermore, the antiseptic agent composition A can contain hyaluronic acid, alpha hydroxy acid and its polyol ester derivatives, ceramides, sterols, N-lauroyl sarcosine (as skin absorption auxiliary agents), beta-carotene, or alantolactone as moisturizing components.

The amount of glycerin hydroxy fatty acid monoester contained in the item to be antisepticized is not particularly limited; in order to effectively produce the intended antiseptic effects, the amount of glycerin hydroxy fatty acid monoester normally falls within a range of 0.001 to 10 weight percent, and preferably a range of 0.01 to 1 weight percent. The glycerin hydroxy fatty acid monoester is known as a moisturizing component; when the glycerin hydroxy fatty acid monoester is compounded as a moisturizing component into a cosmetic, in order to effectively produce the intended moisturizing effects and antiseptic effects, the amount of glycerin hydroxy fatty acid monoester normally falls within a range of 0.1 to 30 weight percent, and preferably a range of 0.5 to 5 weight percent.

The amount of the specific antiseptic agent contained in the item to be antisepticized is not particularly limited; in order to effectively produce the intended antiseptic effects, the amount of the specific antiseptic agent normally falls within a range of 0.01 to 30 weight percent, and preferably a range of 0.1 to 10 weight percent.

When the antiseptic agent composition A of the present invention is compounded into the item to be antisepticized described above, a publicly known apparatus (a paddle mixer, a homo mixer, a homogenizer and the like) that can produce the applications described above can be suitably used. Since the antiseptic agent composition A of the present invention has an excellent compounding property, individual components of the antiseptic agent composition A are not separated out as crystals from the produced various items to be antisepticized.

[Antiseptic Agent Composition B]

As described above, the antiseptic agent composition B of the present invention is characterized in that the antiseptic agent composition B contains a glycerin hydroxy fatty acid monoester and an aromatic antiseptic agent.

The glycerin hydroxy fatty acid monoester, as described above, refers to a compound that is obtained by binding one molecule of glycerin to one molecule of hydroxy fatty acid having 8 to 18 carbon atoms through an ester bond. Examples of the fatty acid of the said glycerin hydroxy fatty acid monoester include: a ricinoleic acid; a 12-hydroxystearic acid; 10-hydroxyundecanoic acid; 9-hydroxyundecanoic acid; 8-hydroxyundecanoic acid; 5-hydroxydodecanoic acid; 5-hydroxyundecanoic acid; 5-hydroxydecanoic acid; 4-hydroxydodecanoic acid; 4-hydroxyundecanoic acid; 4-hydroxydecanoic acid; 9-hydroxy-2-decenoic acid; and 5-hydroxy-7-decenoic acid; one of these compounds or a mixture of two or more of the same can be used. Among them, a glycerin ricinoleic acid monoester is preferable in that its antiseptic property is particularly excellent.

The aromatic antiseptic agent refers to an agent that has a benzene ring and an antiseptic property by itself and that has an enhanced antiseptic property in that, when the aromatic antiseptic agent is compounded together with the glycerin hydroxy fatty acid monoester described above into an item to be antisepticized described later, as compared with a case where each of the above two compounds is individually used, the decrease in the remaining number of at least one species of bacteria is accelerated (in other words, an agent that produces a synergistic effect of an antiseptic property against at least one species of bacteria). Examples of this type of aromatic antiseptic agent include: p-hydroxybenzoate esters such as methylparaben, ethylparaben, propylparaben and butylparaben; and phenoxyethanol, isopropyl methylphenol, benzoic acid, sodium benzoate and potassium benzoate; and salicylic acid; one of these compounds or a mixture of two or more of the same can be used.

The antiseptic agent composition B of the present invention contains a glycerin hydroxy fatty acid monoester and the aromatic antiseptic agent. When the antiseptic agent composition of the present invention is compounded into an item to be antisepticized that can be selected from, for example, food products, tableware, perfume cosmetics, cosmetics, external preparations for skin, oral hygiene products, quasi drugs, daily hygiene products, clothing, paints, and pet hygiene products, the antiseptic agent composition has an excellent antiseptic property against gram-positive bacteria, gram-negative bacteria and yeast, and further has significant effects (synergistic effects) of the antiseptic property against, for example, gram-negative bacteria and yeast as compared with the total effects of the antiseptic properties of individual components. As described above, in the present invention, the glycerin hydroxy fatty acid monoester and the aromatic antiseptic agent are used together, and thus it is possible to reduce the amount of aromatic antiseptic agent used and therefore increase the safety of the antiseptic agent composition B.

The antiseptic agent composition B of the present invention can be widely applied to cosmetics, drugs, quasi drugs and the like that are externally applied, and can be in various forms, such as a water solution form, a soluble form, an emulsion form, an oil form, a gel form, a paste form, an ointment form, or an aerosol form. With respect to basic skin cosmetics, the antiseptic agent composition B in the various forms described above can be widely applied to face washes, lotions, milky lotions, creams, gels, essences (beauty essences), packs and masks, and the like. Furthermore, with respect to makeup cosmetics, the antiseptic agent composition B in various forms described above can be widely applied to foundations, mascara, nail enamel, lipsticks and the like. Moreover, with respect to hair care cosmetics, the antiseptic agent composition B in various forms described above can be widely applied to shampoos, rinses, hair growth drugs, and the like. With respect to drugs and quasi drugs, the antiseptic agent composition B can be widely applied to various types of ointments and the like. With respect to oral hygiene products, the antiseptic agent composition B can be applied to mouthwashes, toothpastes, mouth fresheners, tablet candies, sheet-shaped films, and the like. The forms and applications of the antiseptic agent composition B according to the present invention are not limited to those forms and applications described above.

The antiseptic agent composition B of the present invention may consist only of the above glycerin hydroxy fatty acid monoester and the aromatic antiseptic agent; the antiseptic agent composition B can widely contain commonly known base components according to those forms and applications described above in the range in which the intended effects of the present invention are not ruined by containing the base components. Examples of other components that can be contained include purified water, ethanol, glycerin, propylene glycol, 1,3-butylene glycol, polyethylene glycol, alcohols having linear-chain and branched-chain alkyls or alkenyls, liquid paraffins, vaseline, lanolin, dimethyl polysiloxane, higher alcohol higher fatty acid esters, higher fatty acids, animal and vegetable oils and fats, synthetic ester oils, silicones, various surface acting agents, sequestering agents (chelating agents), water-soluble polymers, thickening agents, various powder components, color agents, perfumes, antioxidizing agents, ultraviolet absorbing agents and montmorillonite. Furthermore, the antiseptic agent composition B can contain hyaluronic acid, alpha hydroxy acid and its polyol ester derivatives, ceramides, sterols, N-lauroyl sarcosine (as skin absorption auxiliary agents), beta-carotene, alantolactone, and the like as moisturizing components.

The amount of glycerin hydroxy fatty acid monoester contained in the item to be antisepticized is not particularly limited; in order to effectively produce the intended antiseptic effects, the amount of glycerin hydroxy fatty acid monoester normally falls within a range of 0.001 to 10 weight percent, and preferably a range of 0.01 to 1 weight percent. The glycerin hydroxy fatty acid monoester is known as a moisturizing component; when the glycerin hydroxy fatty acid monoester is compounded as a moisturizing component into a cosmetic, in order to effectively produce the intended moisturizing effects and antiseptic effects, the amount of glycerin hydroxy fatty acid monoester normally falls within a range of 0.1 to 30 weight percent, and preferably a range of 0.5 to 5 weight percent.

The amount of the aromatic antiseptic agent contained in the item to be antisepticized is not particularly limited; in order to effectively produce the intended antiseptic effects, the amount of the aromatic antiseptic agent normally falls within a range of 0.01 to 30 weight percent, and preferably a range of 0.1 to 10 weight percent.

When the antiseptic agent composition B of the present invention is compounded into the item to be antisepticized described above, a publicly known apparatus (a paddle mixer, a homo mixer, a homogenizer and the like) that can produce the applications described above can be suitably used. Since the antiseptic agent composition B of the present invention has an excellent compounding property, individual components of the antiseptic agent composition B are not separated out as crystals from the produced various items to be antisepticized.

[Antiseptic Agent Composition C]

As described above, the antiseptic agent composition C of the present invention is characterized in that the antiseptic agent composition C contains a glycerin hydroxy fatty acid monoester and a chelating agent.

The glycerin hydroxy fatty acid monoester, as described above, refers to a compound that is obtained by binding one molecule of glycerin to one molecule of hydroxy fatty acid having 8 to 18 carbon atoms through an ester bond. Examples of the fatty acid of the said glycerin hydroxy fatty acid monoester include: a ricinoleic acid; a 12-hydroxystearic acid; 10-hydroxyundecanoic acid; 9-hydroxyundecanoic acid; 8-hydroxyundecanoic acid; 5-hydroxydodecanoic acid; 5-hydroxyundecanoic acid; 5-hydroxydecanoic acid; 4-hydroxydodecanoic acid; 4-hydroxyundecanoic acid; 4-hydroxydecanoic acid; 9-hydroxy-2-decenoic acid; and 5-hydroxy-7-decenoic acid; one of these compounds or a mixture of two or more of the same can be used. Among them, a glycerin ricinoleic acid monoester is preferable in that its antiseptic property is particularly excellent.

The chelating agent that can be used in the present invention refers to an agent that has little antiseptic property by itself and that has an enhanced antiseptic property in that, when the antiseptic agent together with the glycerin hydroxy fatty acid monoester described above is contained in an item to be antisepticized described later, as compared with a case where each of the above two compounds is individually used, the decrease in the remaining number of at least one species of bacteria is accelerated (in other words, an agent that produces a synergistic effect of an antiseptic property against at least one species of bacteria). As this type of chelating agent, an aminocarboxylic acid chelating agent is preferably used. Examples thereof include ethylenediaminetetraacetic acid (EDTA), hydroxyethylethylenediaminetriacetic acid (HEDTA), dihydroxyethylethylenediaminediacetic acid (DHEDDA), 1,3-propanediaminetetraacetic acid (1,3PDTA), diethylenetriaminepentaacetic acid (DTPA), triethylenetetraminehexaacetic acid (TTHA), nitrilotriacetic acid (NTA), hydroxyethyliminodiacetic acid (HIMDA), L-aspartic acid-N,N-diacetic acid (ASDA) and salts thereof. One of these compounds or a mixture of two or more of the same can be used. Among them, EDTA and the salts thereof are more preferable.

The antiseptic agent composition C of the present invention contains the glycerin hydroxy fatty acid monoester and the chelating agent described above. When the antiseptic agent composition of the present invention is contained in an item to be antisepticized that can be selected from, for example, food products, tableware, perfume cosmetics, cosmetics, external preparations for skin, oral hygiene products, quasi drugs, daily hygiene products, clothing, paints, and pet hygiene products, the antiseptic agent composition has an excellent antiseptic property against gram-positive bacteria, gram-negative bacteria, yeast and mold, and further has significant effects (synergistic effects) of the antiseptic property against fungi such as yeast and mold as compared with the total effects of the antiseptic properties of individual components. As described above, since, in the present invention, the glycerin hydroxy fatty acid monoester and the chelating agent are contained, it is unnecessary to use a conventional aromatic antiseptic agent, and thus it is possible to increase the safety of the antiseptic agent composition.

The antiseptic agent composition C of the present invention can be widely applied to cosmetics, drugs, quasi drugs and the like that are externally applied, and can be in various forms, such as a water solution form, a soluble form, an emulsion form, an oil form, a gel form, a paste form, an ointment form, or an aerosol form. With respect to basic skin cosmetics, the antiseptic agent composition C in various forms described above can be widely applied to face washes, lotions, milky lotions, creams, gels, essences (beauty essences), and packs and masks and the like. Furthermore, with respect to makeup cosmetics, the antiseptic agent composition C in various forms described above can be widely applied to foundations, mascara, nail enamel, lipsticks and the like. Moreover, with respect to hair care cosmetics, the antiseptic agent composition C in various forms described above can be widely applied to shampoos, rinses, hair growth drugs, and the like. With respect to drugs and quasi drugs, the antiseptic agent composition C can be widely applied to various types of ointments and the like. With respect to oral hygiene products, the antiseptic agent composition C can be applied to mouthwashes, toothpastes, mouth fresheners, tablet candies, sheet-shaped films, and the like. The forms and applications of the antiseptic agent composition C according to the present invention are not limited to those forms and applications described above.

The antiseptic agent composition C of the present invention may consist only of the above glycerin hydroxy fatty acid monoester and the chelating agent; the antiseptic agent composition C can widely contain commonly known base components according to those forms and applications described above in the range in which the intended effects of the present invention are not ruined by containing the base components. Examples of other components that can be contained include purified water, ethanol, glycerin, propylene glycol, 1,3-butylene glycol, polyethylene glycol, alcohols having linear-chain and branched-chain alkyls or alkenyls, liquid paraffins, vaseline, lanolin, dimethyl polysiloxane, higher alcohol higher fatty acid esters, higher fatty acids, animal and vegetable oils and fats, synthetic ester oils, silicones, various surface acting agents, water-soluble polymers, thickening agents, various powder components, color agents, perfumes, antioxidizing agents, ultraviolet absorbing agents and montmorillonite. Furthermore, the antiseptic agent composition B can contain hyaluronic acid, alpha hydroxy acid and its polyol ester derivatives, ceramides, sterols, N-lauroyl sarcosine (as skin absorption auxiliary agents), beta-carotene, alantolactone, and the like as moisturizing components.

The amount of glycerin hydroxy fatty acid monoester contained in the item to be antisepticized is not particularly limited; in order to effectively produce the intended antiseptic effects, the amount of glycerin hydroxy fatty acid monoester normally falls within a range of 0.001 to 10 weight percent, and preferably a range of 0.01 to 1 weight percent. The glycerin hydroxy fatty acid monoester is known as a moisturizing component; when the glycerin hydroxy fatty acid monoester is compounded as a moisturizing component into a cosmetic, in order to effectively produce the intended moisturizing effects and antiseptic effects, the amount of glycerin hydroxy fatty acid monoester normally falls within a range of 0.1 to 30 weight percent, and preferably a range of 0.5 to 5 weight percent.

The amount of the chelating agent contained in the item to be antisepticized is not particularly limited; in order to effectively produce the intended antiseptic effects, the amount of the specific antiseptic agent normally falls within a range of 0.01 to 30 weight percent, and preferably a range of 0.1 to 10 weight percent.

When the antiseptic agent composition C of the present invention is compounded into the item to be antisepticized, a publicly known apparatus (a paddle mixer, a homo mixer, a homogenizer and the like) that can produce the applications described above can be suitably used. Since the antiseptic agent composition C of the present invention has an excellent compounding property, individual components of the antiseptic agent composition C are not separated out as crystals from the produced various items to be antisepticized.

Although the antiseptic agent compositions A to C have been described above, in the present invention, any of the antiseptic agent compositions A to C can be individually used or a combination of two or more of the same can be selected and used as appropriate in the range in which the effects of the present invention are not prevented.

EXAMPLES

Although the present invention will be more specifically described below using examples, these examples are not intended to limit the present invention.

(Evaluation of the Antiseptic Agent Composition A)

1. Antiseptic Property Evaluation Test for Lotions

The antiseptic agent composition A containing a glycerin ricinoleic acid monoester and 1,2-octanediol or a glycerin ricinoleic acid monoester and a glycerin caprylic acid monoester was compounded according to a formula shown in table 1, thus lotions for examples 1 and 2 and comparative examples 1 to 4 were made and the antiseptic property was evaluated by a challenge test.

TABLE 1

| | Content weight (%) | | | | | |
| --- | --- | --- | --- | --- | --- | --- |
| Components | Example 1 | Example 2 | Comparative example 1 | Comparative example 2 | Comparative example 3 | Comparative example 4 |
| 1,3-butylene glycol | 6.0 | 6.0 | 6.0 | 6.0 | 6.0 | 6.0 |
| Glycerin | 4.0 | 4.0 | 4.0 | 4.0 | 4.0 | 4.0 |
| Polyethylene glycol 1000 *a) | 1.0 | 1.0 | 1.0 | 1.0 | 1.0 | 1.0 |
| POE (60) hydrogenated castor oil *b) | 0.3 | 0.3 | 0.3 | 0.3 | 0.3 | 0.3 |
| Glycerin ricinoleic | 0.15 | 0.15 | 0.15 | — | — | — |

TABLE 1-continued

| Components | Content weight (%) | | | | | |
|---|---|---|---|---|---|---|
| | Example 1 | Example 2 | Comparative example 1 | Comparative example 2 | Comparative example 3 | Comparative example 4 |
| acid mono-ester *c) | | | | | | |
| 1,2-octanediol | 0.15 | — | — | 0.15 | — | — |
| Glycerin caprylic acid monoester *d) | — | 0.15 | — | — | 0.15 | — |
| Water | Remaining part | Remaining part | Remaining part | Remaining part | Remaining part | Remaining part |

*a) Polyethylene glycol 1000 made by Wako Pure Chemical Industries, Ltd.
*b) Noigen HC-600 made by Dai-Ichi Kogyo Seiyaku Co., Ltd.
*c) Ricinolex made by Taiyo Corporation
*d) Sunsoft No. 700P made by Taiyo Kagaku Co., Ltd.

As bacteria to be tested, common bacteria, that is, *S. aureus*, JCM2151; *P. aeruginosa*, NBRC13275; and *E. coli*, JCM1649 were used. As yeast, *C. albicans*, NBRC1594 was used. A culture solution obtained by previously culturing these bacteria was prepared into about $10^6$ cells/ml, and it was used as a bacterial suspension. The number of bacteria was determined by a colony count method.

20 grams each of the lotions for examples 1 and 2 and comparative examples 1 to 4 was put into a 50 ml vial container sterilized by an autoclave, 0.2 ml of the bacterial suspension was inoculated, and cultivation was performed at 25° C. With respect to the remaining number of bacteria in the test samples, 0.5 grams of each of the test samples was taken at the time of the inoculation, after one hour, after one day and after seven days, the solution obtained by dilution with saline solution was applied to an agar medium and cultured for 24 hours and the number of bacteria in the test samples was calculated. The results are shown in tables 2 to 5.

TABLE 2

| | | *E. coli* (cells/g) | | | |
|---|---|---|---|---|---|
| | | At the time of the inoculation | 1 hour | 1 day | 7 days |
| Example | 1 | $9.1 \times 10^5$ | $1.4 \times 10^5$ | $1.4 \times 10^4$ | 0 |
| | 2 | | 0 | 0 | 0 |
| Comparative example | 1 | | $1.8 \times 10^5$ | $1.0 \times 10^5$ | $3.0 \times 10^3$ |
| | 2 | | $2.4 \times 10^5$ | $1.2 \times 10^5$ | 0 |
| | 3 | | $2.3 \times 10^5$ | $1.3 \times 10^4$ | 0 |
| | 4 | | $4.3 \times 10^5$ | $2.2 \times 10^5$ | $9.6 \times 10^4$ |

TABLE 3

| | | *P. aeruginosa* (cells/g) | | | |
|---|---|---|---|---|---|
| | | At the time of the inoculation | 1 hour | 1 day | 7 days |
| Example | 1 | $2.8 \times 10^6$ | $2.2 \times 10^5$ | $1.0 \times 10^4$ | 0 |
| | 2 | | 0 | 0 | 0 |
| Comparative example | 1 | | $2.3 \times 10^5$ | $8.7 \times 10^5$ | $6.9 \times 10^3$ |
| | 2 | | $3.4 \times 10^5$ | $2.1 \times 10^5$ | 0 |
| | 3 | | $4.1 \times 10^5$ | $6.1 \times 10^3$ | 0 |
| | 4 | | $3.1 \times 10^5$ | $2.5 \times 10^6$ | $2.5 \times 10^5$ |

TABLE 4

| | | *C. albicans* (cells/g) | | | |
|---|---|---|---|---|---|
| | | At the time of the inoculation | 1 hour | 1 day | 7 days |
| Example | 1 | $1.1 \times 10^6$ | $1.1 \times 10^4$ | 0 | 0 |
| | 2 | | $2.1 \times 10^4$ | 0 | 0 |
| Comparative example | 1 | | $1.4 \times 10^4$ | $3.0 \times 10^5$ | $1.4 \times 10^5$ |
| | 2 | | $1.6 \times 10^6$ | $9.5 \times 10^5$ | $2.4 \times 10^6$ |
| | 3 | | $4.7 \times 10^5$ | $1.1 \times 10^5$ | 0 |
| | 4 | | $1.6 \times 10^6$ | $2.9 \times 10^6$ | $9.6 \times 10^6$ |

TABLE 5

| | | *S. aureus* (cells/g) | | | |
|---|---|---|---|---|---|
| | | At the time of the inoculation | 1 hour | 1 day | 7 days |
| Example | 1 | $4.4 \times 10^6$ | $2.2 \times 10^6$ | 0 | 0 |
| | 2 | | $2.1 \times 10^6$ | 0 | 0 |
| Comparative example | 1 | | $2.4 \times 10^6$ | 0 | 0 |
| | 2 | | $2.4 \times 10^6$ | $5.7 \times 10^6$ | $5.7 \times 10^4$ |
| | 3 | | $2.2 \times 10^6$ | $5.3 \times 10^6$ | $4.3 \times 10^2$ |
| | 4 | | $2.0 \times 10^6$ | $6.4 \times 10^6$ | $6.4 \times 10^5$ |

Table 2 shows that, when the lotion (example 1) in which a glycerin ricinoleic acid monoester and 1,2-octanediol were used together was compared with the lotions (comparative examples 1 and 2) in which each of the above-mentioned components was individually used, in the case where the above two compounds were used together, the decrease in the remaining number of bacteria was accelerated and the antiseptic property against *E. coli* was enhanced.

Table 2 also shows that the synergistic effect of the antiseptic property produced by the above simultaneous use of two components was more significant when the glycerin ricinoleic acid monoester and the glycerin caprylic acid monoester were used together (see the results of example 2 and comparative examples 1 and 3 in table 2).

With respect to the antiseptic property against *P. aeruginosa*, the same result as described above was shown (see the results of example 1 and comparative examples 1 and 2 and the results of example 2 and comparative examples 1 and 3 in table 3). Furthermore, with respect to the antiseptic property against *C. albicans*, the synergistic effect of the antiseptic property produced when a glycerin ricinoleic acid monoester and 1,2-octanediol (or a glycerin caprylic acid monoester) were used together was more significant than the above-described results of the antiseptic property against *E. coli* and

*P. aeruginosa* (see the results of example 1 and comparative examples 1 and 2 and the results of example 2 and comparative examples 1 and 3 in table 4).

With respect to *S. aureus*, even when only the glycerin ricinoleic acid monoester was used, since the antiseptic property of the lotion was too strong, the synergistic effect of the antiseptic property produced when the glycerin ricinoleic acid monoester and 1,2-octanediol or the glycerin caprylic acid monoester were used together was not found (see the results of example 1 and comparative examples 1 and 2 and the results of example 2 and comparative examples 1 and 3 in table 5). However, it has been recognized that the products according to the present invention (examples 1 and 2) have the excellent antiseptic property against *S. aureus*.

It has been found from the above results that the lotion in which the glycerin ricinoleic acid monoester and 1,2-octanediol (or the glycerin caprylic acid monoester) were used together has the excellent antiseptic property against gram-positive bacteria, gram-negative bacteria and yeast, and that the antiseptic property against gram-negative bacteria, and yeast clearly shows significant effects (synergistic effects) as compared with the effects obtained by combining the antiseptic properties of the individual components.

2. Compounding Property

The compounding property of the cosmetic composition according to the present invention was examined.

2-1. Lotion (Formula)

| | |
|---|---|
| Glycerin | 5.00 weight % |
| Dipropylene glycol (DPG) | 3.00 |
| POE (60) hydrogenated castor oil *a) | 0.60 |
| Citric acid Na | 0.15 |
| Citric acid | 0.01 |
| Glycine | 0.20 |
| Alanine | 0.10 |
| Hyaluronic acid Na | 0.01 |
| Glycerin ricinoleic acid monoester *b) | 0.15 |
| 1,2-octanediol | 0.15 |
| Water | Remaining part |

*a): Noigen HC-600 made by Dai-Ichi Kogyo Seiyaku Co., Ltd.
*b): Ricinolex made by Taiyo Corporation (Formulation Method)

Glycerine, DPG, POE (60) hydrogenated castor oil, glycerin ricinoleic acid monoester, and 1,2-octanediol were mixed and dissolved by being heated to 70° C. (the resulting mixture was referred to as the antiseptic agent composition A (the product according to the present invention)). On the other hand, citric acid Na, citric acid, glycine, alanine, hyaluronic acid Na, and water were mixed at room temperature (the resulting mixture was referred to as a mixture A). Then, the product according to the present invention and the mixture A were mixed at 50° C., and thus a lotion was obtained.

(Compounding Property)

The product according to the present invention was easily immingled with other components. Turbidity or precipitation was not found in the obtained lotion.

2-2. Milky Lotion (Formula)

| | |
|---|---|
| Cetanol | 1.00 weight % |
| Squalane | 4.00 |
| Stearic acid | 1.00 |
| Polyethylene glycol monostearate (25EO) *a) | 3.20 |
| Glycerin stearic acid monoester *b) | 1.00 |
| Glycerin ricinoleic acid monoester *c) | 0.15 |
| 1,2-octanediol | 0.15 |
| γ-tocopherol | 0.05 |
| BHT (antioxidizing agent) | 0.01 |
| 1,3-butanediol | 3.00 |
| Propylene glycol | 7.00 |
| Carboxy vinyl polymer | 0.20 |
| Potassium hydroxide | 0.20 |
| Purified water | Remaining part |

*a): Polyethylene glycol monostearate (n = 25) made by Tokyo Chemical Industry Co., Ltd.
*b): Monostearate glycerol made by Wako Pure Chemical Industries, Ltd.
*c) Ricinolex made by Taiyo Corporation (Formulation Method)

Cetanol, squalane, stearic acid, γ-tocopherol, BHT, polyethylene glycol monostearate (25EO), the glycerin stearic acid monoester, the glycerin ricinoleic acid monoester, and 1,2-octanediol were mixed and dissolved by being heated to 70° C. (the resulting mixture was referred to as the antiseptic agent composition A (the product according to the present invention)). On the other hand, 1,3-butanediol, propylene glycol, carboxy vinyl polymer, and potassium hydroxide were mixed at room temperature (the resulting mixture was referred to as a mixture B). Then, the product according to the present invention and the mixture B were mixed and heated to 60° C., and were vigorously stirred and emulsified while being added in small quantities to the purified water, and thus a milky lotion was obtained.

(Compounding Property)

The product according to the present invention was immediately immingled with other components. Separation or precipitation was not found in the obtained milky lotion.

(Evaluation of the Antiseptic Agent Composition B)

3. Antiseptic Property Evaluation Test for Lotions

The antiseptic agent composition B containing the glycerin ricinoleic acid monoester and methylparaben or the glycerin ricinoleic acid monoester and phenoxyethanol was compounded according to a formula shown in table 6, thus lotions for examples 3 and 4 and comparative examples 5 to 10 were made and the antiseptic property was evaluated by a challenge test.

TABLE 6

| Components | Content (weight %) | | | | | | | |
|---|---|---|---|---|---|---|---|---|
| | Example 3 | Example 4 | Comparative example 5 | Comparative example 6 | Comparative example 7 | Comparative example 8 | Comparative example 9 | Comparative example 10 |
| 1,3-butylene glycol | 6.0 | 6.0 | 6.0 | 6.0 | 6.0 | 6.0 | 6.0 | 6.0 |
| Glycerin | 4.0 | 4.0 | 4.0 | 4.0 | 4.0 | 4.0 | 4.0 | 4.0 |
| Polyethylene glycol 1000 *a) | 1.0 | 1.0 | 1.0 | 1.0 | 1.0 | 1.0 | 1.0 | 1.0 |
| POE (60) hydrogenated castor oil *b) | 0.3 | 0.3 | 0.3 | 0.3 | 0.3 | 0.3 | 0.3 | 0.3 |
| Glycerin ricinoleic acid mono-ester *c) | 0.15 | 0.15 | 0.15 | — | — | — | — | — |
| Methylparaben | 0.15 | — | — | 0.15 | — | 0.30 | — | — |
| Phenoxyethanol | — | 0.15 | — | — | 0.15 | — | 0.30 | — |
| Water | Remaining part | Remaining part | Remaining part | Remaining part | Remaining part | Remaining part | Remaining part | Remaining part |

*a) Polyethylene glycol 1000 made by Wako Pure Chemical Industries, Ltd.
*b) Noigen HC-600 made by Dai-Ichi Kogyo Seiyaku Co., Ltd.
*c) Ricinolex made by Taiyo Corporation As bacteria to be tested, common bacteria, that is, *S. aureus*, JCM2151; *P. aeruginosa*, NBRC13275; and *E. coli*, JCM1649 were used. As yeast, *C. albicans*, NBRC1594 was used. A culture solution obtained by previously culturing these bacteria was prepared into about $10^6$ cells/ml, and it was used as a bacterial suspension. The number of bacteria was determined by a colony count method.

20 grams each of the lotions for examples 3 and 4 and comparative examples 5 to 10 was put into a 50 ml vial container sterilized by an autoclave, 0.2 ml of the bacterial suspension was inoculated, and cultivation was performed at 25° C. With respect to the remaining number of bacteria in the test samples, 0.5 grams of each of the test samples was taken at the time of the inoculation, after one hour, after one day, after seven days, and after 14 days, the solution obtained by dilution with saline solution was applied to an agar medium and cultured for 24 hours and the number of bacteria in the test samples was calculated. The results are shown in tables 7 to 10.

TABLE 7

| | | *E. coli* (cells/g) | | | | |
|---|---|---|---|---|---|---|
| | | At the time of the inoculation | 1 hour | 1 day | 7 days | 14 days |
| Example | 3 | $3.0 \times 10^6$ | 0 | 0 | 0 | 0 |
| | 4 | | $4.1 \times 10^5$ | $3.0 \times 10^5$ | 0 | 0 |
| Comparative example | 5 | | $8.0 \times 10^5$ | $4.6 \times 10^5$ | $3.5 \times 10^5$ | $1.1 \times 10^5$ |
| | 6 | | $1.8 \times 10^6$ | $2.8 \times 10^5$ | 0 | 0 |
| | 7 | | $2.7 \times 10^6$ | $1.1 \times 10^6$ | $1.8 \times 10^4$ | 0 |
| | 8 | | $5.5 \times 10^5$ | $3.3 \times 10^3$ | 0 | 0 |
| | 9 | | $2.1 \times 10^6$ | $4.7 \times 10^5$ | 0 | 0 |
| | 10 | | $2.1 \times 10^6$ | $3.6 \times 10^6$ | $1.3 \times 10^5$ | $1.4 \times 10^5$ |

TABLE 8

| | | *P. aeruginosa* (cells/g) | | | | |
|---|---|---|---|---|---|---|
| | | At the time of the inoculation | 1 hour | 1 day | 7 days | 14 days |
| Example | 3 | $6.4 \times 10^6$ | $3.4 \times 10^3$ | 0 | 0 | 0 |
| | 4 | | $2.9 \times 10^5$ | $6.0 \times 10^4$ | 0 | 0 |
| Comparative example | 5 | | $8.6 \times 10^5$ | $2.3 \times 10^5$ | $5.6 \times 10^4$ | $1.9 \times 10^3$ |
| | 6 | | $4.1 \times 10^5$ | $1.2 \times 10^4$ | 0 | 0 |
| | 7 | | $1.4 \times 10^6$ | $4.2 \times 10^5$ | $1.5 \times 10^5$ | 0 |
| | 8 | | $6.7 \times 10^4$ | 0 | 0 | 0 |
| | 9 | | $8.5 \times 10^5$ | $2.0 \times 10^5$ | 0 | 0 |
| | 10 | | $1.9 \times 10^6$ | $9.9 \times 10^5$ | $1.5 \times 10^5$ | $3.3 \times 10^4$ |

TABLE 9

| | | *C. albicans* (cells/g) | | | | |
|---|---|---|---|---|---|---|
| | | At the time of the inoculation | 1 hour | 1 day | 7 days | 14 days |
| Example | 3 | $3.4 \times 10^5$ | $2.0 \times 10^5$ | $1.1 \times 10^3$ | 0 | 0 |
| | 4 | | $1.7 \times 10^5$ | $1.9 \times 10^4$ | $2.9 \times 10^3$ | 0 |
| Comparative example | 5 | | $1.8 \times 10^5$ | $2.8 \times 10^4$ | $1.2 \times 10^4$ | $5.4 \times 10^3$ |
| | 6 | | $6.2 \times 10^5$ | $4.6 \times 10^5$ | 0 | 0 |
| | 7 | | $2.7 \times 10^5$ | $3.4 \times 10^5$ | $1.0 \times 10^5$ | $6.0 \times 10^4$ |
| | 8 | | $4.3 \times 10^5$ | $4.9 \times 10^5$ | 0 | 0 |
| | 9 | | $3.6 \times 10^5$ | $5.0 \times 10^4$ | $2.5 \times 10^3$ | 0 |
| | 10 | | $3.0 \times 10^5$ | $2.7 \times 10^5$ | $1.5 \times 10^5$ | $1.4 \times 10^4$ |

TABLE 10

| | | S.aursus (cells/g) | | | |
|---|---|---|---|---|---|
| | | At the time of the inoculation | 1 hour | 1 day | 7 days | 14 days |
| Example | 3 | $1.5 \times 10^6$ | $2.8 \times 10^6$ | 0 | 0 | 0 |
| | 4 | | $1.3 \times 10^6$ | 0 | 0 | 0 |
| Comparative example | 5 | | $1.3 \times 10^6$ | 0 | 0 | 0 |
| | 6 | | $2.3 \times 10^6$ | $3.7 \times 10^5$ | 0 | 0 |
| | 7 | | $1.1 \times 10^6$ | $7.9 \times 10^5$ | 0 | 0 |
| | 8 | | $2.2 \times 10^6$ | $2.4 \times 10^4$ | 0 | 0 |
| | 9 | | $1.9 \times 10^5$ | $7.6 \times 10^5$ | 0 | 0 |
| | 10 | | $1.6 \times 10^6$ | $7.3 \times 10^5$ | 0 | 0 |

Table 7 shows that, when the lotion (example 4) in which the glycerin ricinoleic acid monoester and phenoxyethanol were used together was compared with the lotions (comparative examples 5 and 7) in which each of the above-mentioned components was individually used, in the case where the above two compounds were used together, the decrease in the remaining number of bacteria was accelerated after seven days and the antiseptic property against $E.$ $coli$ was enhanced.

Table 7 also shows that the synergistic effect of the antiseptic property produced by the above simultaneous use of two components was more significant when the glycerin ricinoleic acid monoester and methylparaben were used together (see the results of example 3 and comparative examples 5 and 6 in table 7). Specifically, it has been found that the antiseptic property against $E.$ $coli$ was enhanced one hour after the inoculation of $E.$ $coli$.

With respect to the antiseptic property against $P.$ $aeruginosa$ and $C.$ $albicans$, substantially the same result as described above was shown. First, with respect to the antiseptic property against $P.$ $aeruginosa$, it has been found that, when the lotions (example 4 in table 8) in which the glycerin ricinoleic acid monoester and phenoxyethanol were used together were compared with the lotions (comparative examples 5 and 7 in table 8) in which each of the above-mentioned components was individually used, in the case where the above two compounds were used together, the decrease in the remaining number of bacteria was accelerated and the antiseptic property against $P.$ $aeruginosa$ was enhanced after seven days. Moreover, when the lotion (example 3 in table 8) in which the glycerin ricinoleic acid monoester and methylparaben were used together was compared with the lotions (comparative examples 5 and 6 in table 8) in which each of the above-mentioned components was individually used, in the case where the above two compounds were used together, the decrease in the remaining number of bacteria was facilitated and the antiseptic property against $P.$ $aeruginosa$ was enhanced after one hour.

With respect to the antiseptic property against $C.$ $albicans$, it has been found that, when the lotion (example 4 in table 9) in which the glycerin ricinoleic acid monoester and phenoxyethanol were used together was compared with the lotions (comparative examples 5 and 7 in table 9) in which each of the above-mentioned components was individually used, in the case where the above two compounds were used together, the decrease in the remaining number of bacteria was accelerated and the antiseptic property against $C.$ $albicans$ was enhanced after fourteen days. Moreover, when the lotion (example 3 in table 9) in which the glycerin ricinoleic acid monoester and methylparaben were used together was compared with the lotions (comparative examples 5 and 6 in table 9) in which each of the above-mentioned components was individually used, in the case where the above two compounds were used together, the decrease in the remaining number of bacteria was accelerated and the antiseptic property against $C.$ $albicans$ was enhanced after one day.

With respect to $S.$ $aureus$, even when only the glycerin ricinoleic acid monoester was used, since the antiseptic property of the lotion was too strong, the synergistic effect of the antiseptic property produced when the glycerin ricinoleic acid monoester and methylparaben or phenoxyethanol were used together was not found (see the results of example 3 and comparative examples 5 and 6 and the results of example 4 and comparative examples 5 and 7 in table 10). However, it has been recognized that the products according to the present invention (examples 3 and 4) have the excellent antiseptic property against $S.$ $aureus$.

It has been found from the above results that the lotion in which the glycerin ricinoleic acid monoester and methylparaben or phenoxyethanol were used together has the excellent antiseptic property against gram-positive bacteria, gram-negative bacteria and yeast, and that the antiseptic property against gram-negative bacteria and yeast clearly shows significant effects (synergistic effects) as compared with the effects obtained by combining the antiseptic properties of the individual components.

4. Compounding Property

The compounding property of the cosmetic composition according to the present invention was examined.

4-1. Lotion (Formula)

| | |
|---|---|
| Glycerin | 5.00 weight % |
| Dipropylene glycol (DPG) | 3.00 |
| POE (60) hydrogenated castor oil *a) | 0.60 |
| Citric acid Na | 0.15 |
| Citric acid | 0.01 |
| Glycine | 0.20 |
| Alanine | 0.10 |
| Hyaluronic acid Na | 0.01 |
| Glycerin ricinoleic acid monoester *b) | 0.30 |
| Phenoxyethanol | 0.30 |
| Water | Remaining part |

*a): Noigen HC-600 made by Dai-Ichi Kogyo Seiyaku Co., Ltd.
*b): Ricinolex made by Taiyo Corporation (Formulation Method)

Glycerine, DPG, POE (60) hydrogenated castor oil, glycerin ricinoleic acid monoester, and phenoxyethanol were mixed and dissolved by being heated to 70° C. (the resulting mixture was referred to as the antiseptic agent composition B (the product according to the present invention)). On the other hand, citric acid Na, citric acid, glycine, alanine, hyaluronic acid Na, and water were mixed at room temperature (the resulting mixture was referred to as a mixture A). Then, the product according to the present invention and the mixture A were mixed at 50° C., and thus a lotion was obtained.

(Compounding Property)

The product according to the present invention was easily immingled with other components. Turbidity or precipitation was not found in the obtained lotion.

4-2. Milky Lotion (Formula)

| | |
|---|---|
| Cetanol | 1.00 weight % |
| Squalane | 4.00 |

-continued

| | |
|---|---|
| Stearic acid | 1.00 |
| Polyethylene glycol monostearate(25EO) *a) | 3.00 |
| Glycerin stearic acid monoester *b) | 1.00 |
| Glycerin ricinoleic acid monoester *c) | 0.30 |
| Phenoxyethanol | 0.30 |
| γ-tocopherol | 0.05 |
| BHT (antioxidizing agent) | 0.01 |
| 1,3-butanediol | 3.00 |
| Propylene glycol | 7.00 |
| Carboxy vinyl polymer | 0.20 |
| Potassium hydroxide | 0.20 |
| Purified water | Remaining part |

*a): Polyethylene glycol monostearate (n = 25) made by Tokyo Chemical Industry Co., Ltd.
*b): Monostearate glycerol made by Wako Pure Chemical Industries, Ltd.
*c) Ricinolex made by Taiyo Corporation (Formulation Method)

Cetanol, squalane, stearic acid, γ-tocopherol, BHT, polyethylene glycol monostearate (25EO), the glycerin stearic acid monoester, the glycerin ricinoleic acid monoester, and phenoxyethanol were mixed and dissolved by being heated to 70° C. (the resulting mixture was referred to as the antiseptic agent composition B (the product according to the present invention)). On the other hand, 1,3-butanediol, propylene glycol, carboxy vinyl polymer, and potassium hydroxide were mixed at room temperature (the resulting mixture was referred to as a mixture B). Then, the product according to the present invention and the mixture B were mixed and heated to 60° C., and were vigorously stirred and emulsified while being added in small quantities to the purified water, and thus a milky lotion was obtained.

(Compounding Property)

The product according to the present invention was immediately immingled with other components. Turbidity or precipitation was not found in the obtained milky lotion.

(Evaluation of the Antiseptic Agent Composition C)

5. Antiseptic Property Evaluation Test for Lotions

The antiseptic agent composition C containing the glycerin ricinoleic acid monoester and disodium ethylenediaminetetraacetate (EDTA-2Na) was compounded according to a formula shown in table 11, thus lotions for example 5 and comparative examples 11 to 13 were made and the antiseptic property was evaluated by a challenge test.

TABLE 11

| | Content (weight %) | | | |
|---|---|---|---|---|
| Components | Example 5 | Comparative example 11 | Comparative example 12 | Comparative example 13 |
| 1,3-butylene glycol | 6.00 | 6.00 | 6.00 | 6.00 |
| Glycerin | 4.00 | 4.00 | 4.00 | 4.00 |
| Polyethylene glycol 1000 *a) | 1.00 | 1.00 | 1.00 | 1.00 |
| POE (60) hydrogenated castor oil *b) | 0.30 | 0.30 | 0.30 | 0.30 |
| Glycerin ricinoleic acid monoester *c) | 0.30 | 0.30 | — | — |
| Disodium ethylenediamine-tetraacetate | 0.05 | — | 0.05 | — |
| Water | Remaining part | Remaining part | Remaining part | Remaining part |

*a): Polyethylene glycol 1000 made by Wako Pure Chemical Industries, Ltd.
*b): Noigen HC-600 made by Dai-Ichi Kogyo Seiyaku Co., Ltd.
*c): Ricinolex made by Taiyo Corporation As bacteria to be tested, common bacteria, that is, *E. coli*, JCM1649; *S. aureus*, JCM2151; and *A. niger*, JCM10254 were used. As yeast, *C. albicans*, NBRC1594 was used. A culture solution obtained by previously culturing these bacteria was prepared into about $10^4$ to $10^6$ cells/ml, and it was used as a bacterial suspension. The number of bacteria was determined by a colony count method.

20 grams each of the lotions for example 5 and comparative examples 11 to 13 was put into a 50 ml vial container sterilized by an autoclave, 0.2 ml of the bacterial suspension was inoculated, and cultivation was performed at 25° C. With respect to the remaining number of bacteria in the test samples, 0.5 grams of each of the test samples was taken at the time of the inoculation, after one hour, after one day, after seven days, and after 14 days, the solution obtained by dilution with saline solution was applied to an agar medium and cultured for 24 hours and the number of bacteria in the test samples was calculated. The results are shown in tables 12 to 15.

TABLE 12

| | | *E. coli* (cells/g) | | | | |
|---|---|---|---|---|---|---|
| | | At the time of the inoculation | 1 hour | 1 day | 7 days | 14 days |
| Example | 5 | $6.9 \times 10^5$ | $8.4 \times 10^5$ | $3.0 \times 10^5$ | 0 | 0 |
| Comparative example | 11 | | $5.5 \times 10^4$ | $2.6 \times 10^3$ | $2.6 \times 10^3$ | 0 |
| | 12 | | $3.3 \times 10^5$ | $1.2 \times 10^6$ | $5.2 \times 10^5$ | $1.6 \times 10^3$ |
| | 13 | | $1.1 \times 10^6$ | $4.3 \times 10^5$ | $9.3 \times 10^4$ | $2.2 \times 10^4$ |

TABLE 13

| | | *S. aureus* (cells/g) | | | | |
|---|---|---|---|---|---|---|
| | | At the time of the inoculation | 1 hour | 1 day | 7 days | 14 days |
| Example | 5 | $7.4 \times 10^6$ | $1.4 \times 10^6$ | 0 | 0 | 0 |
| Comparative example | 11 | | $2.4 \times 10^6$ | 0 | 0 | 0 |
| | 12 | | $3.0 \times 10^6$ | $3.6 \times 10^6$ | $8.7 \times 10^5$ | $3.6 \times 10^5$ |
| | 13 | | $5.1 \times 10^6$ | $3.0 \times 10^6$ | $1.3 \times 10^3$ | $1.4 \times 10^3$ |

TABLE 14

| | | *C. albicans* (cells/g) | | | | |
|---|---|---|---|---|---|---|
| | | At the time of the inoculation | 1 hour | 1 day | 7 days | 14 days |
| Example | 5 | $2.0 \times 10^5$ | $7.9 \times 10^3$ | 0 | 0 | 0 |
| Comparative example | 11 | | $3.1 \times 10^4$ | $7.9 \times 10^3$ | $6.1 \times 10^3$ | $3.2 \times 10^2$ |
| | 12 | | $2.0 \times 10^5$ | $1.6 \times 10^5$ | $2.5 \times 10^4$ | $4.6 \times 10^3$ |
| | 13 | | $2.3 \times 10^5$ | $8.9 \times 10^4$ | $6.8 \times 10^4$ | $2.9 \times 10^4$ |

TABLE 15

| | | A. niger (cells/g) | | | | |
|---|---|---|---|---|---|---|
| | | At the time of the inoculation | 1 hour | 1 day | 7 days | 14 days |
| Example | 5 | $1.7 \times 10^4$ | $1.5 \times 10^4$ | $7.2 \times 10^3$ | $1.0 \times 10^3$ | 0 |
| Comparative example | 11 | | $1.2 \times 10^4$ | $5.6 \times 10^4$ | $6.4 \times 10^3$ | $4.2 \times 10^3$ |
| | 12 | | $1.4 \times 10^4$ | $1.1 \times 10^4$ | $5.8 \times 10^3$ | $7.6 \times 10^3$ |
| | 13 | | $1.1 \times 10^4$ | $1.2 \times 10^4$ | $1.5 \times 10^4$ | $1.2 \times 10^4$ |

With respect to the antiseptic property against *E. coli*, it has been found that, when the lotion (example 5 in table 12) in which the glycerin ricinoleic acid monoester and EDTA-2Na were used together was compared with the lotions (comparative examples 11 and 12 in table 12) in which each of the above-mentioned components was individually used, in the case where the above two compounds were used together, the remaining number of bacteria became zero and the antiseptic property against *E. coli* was enhanced after seven days.

With respect to the antiseptic property against *C. albicans*, it has been found that, when the lotion (example 5 in table 14) in which the glycerin ricinoleic acid monoester and EDTA-2Na were used together was compared with the lotions (comparative examples 11 and 12 in table 14) in which each of the above-mentioned components was individually used, in the case where the above two compounds were used together, the remaining number of bacteria became zero and the antiseptic property functioned beyond the above-described antiseptic property against *E. coli* described above synergistically after one day.

With respect to the antiseptic property against *A. niger*, it has been found that, when the glycerin ricinoleic acid monoester or EDTA-2Na was individually used, the remaining number of bacteria did not become zero (comparative examples 11 and 12 in table 15) whereas, when the two compounds were used together, the remaining number of bacteria became zero after two weeks (example 5 in table 15).

With respect to *S. aureus*, even when only the glycerin ricinoleic acid monoester was used, since the antiseptic property of the lotion was too strong (comparative example 11 in table 13), the synergistic effect of the antiseptic property produced when the glycerin ricinoleic acid monoester and EDTA-2Na were used together was not found (see example 5 in table 13). However, it has been recognized that the products according to the present invention have the excellent antiseptic property against *S. aureus*.

It has been found from the above results that the lotion in which the glycerin ricinoleic acid monoester and EDTA-2Na were used together has the excellent antiseptic property against gram-positive bacteria, gram-negative bacteria, yeast and mold, and that the antiseptic property against fungi such as yeast and mold clearly shows significant effects (synergistic effects) as compared with the effects obtained by combining the antiseptic properties of the individual components.

6. Compounding Property

The compounding property of the cosmetic composition according to the present invention was examined.

6-1. Lotion
(Formula)

| Glycerin | 5.00 weight % |
|---|---|
| Dipropylene glycol (DPG) | 3.00 |
| POE (60) hydrogenated castor oil *a) | 0.80 |
| Citric acid Na | 0.15 |
| Citric acid | 0.01 |
| Glycine | 0.20 |
| Alanine | 0.10 |
| Hyaluronic acid Na | 0.01 |
| Glycerin ricinoleic acid monoester *b) | 0.30 |
| Disodium ethylenediaminetetraacetate *c) | 0.05 |
| Water | Remaining part |

*a): Noigen HC-600 made by Dai-Ichi Kogyo Seiyaku Co., Ltd.
*b): Ricinolex made by Taiyo Corporation (Formulation Method)

Glycerine, DPG, POE (60) hydrogenated castor oil, and glycerin ricinoleic acid monoester were mixed and dissolved by being heated to 70° C. (the resulting mixture was referred to as the antiseptic agent composition C (the product according to the present invention)). On the other hand, citric acid Na, citric acid, glycine, alanine, hyaluronic acid Na, EDTA-2Na, and water were mixed at room temperature (the resulting mixture was referred to as a mixture B). Then, the product according to the present invention and the mixture B were mixed at 50° C., and thus a lotion was obtained.

(Compounding Property)

The product according to the present invention was easily immingled with other components. Turbidity or precipitation was not found in the obtained lotion.

6-2. Milky Lotion
(Formula)

| Cetanol | 1.00 weight % |
|---|---|
| Squalane | 4.00 |
| Stearic acid | 1.00 |
| Polyethylene glycol monostearate(25EO) *a) | 3.00 |
| Glycerin stearic acid monoester *b) | 1.00 |
| Glycerin ricinoleic acid monoester *c) | 0.30 |
| Disodium ethylenediaminetetraacetate | 0.10 |
| γ-tocopherol | 0.05 |
| BHT (antioxidizing agent) | 0.01 |
| 1,3-butanediol | 3.00 |
| Propylene glycol | 7.00 |
| Carboxy vinyl polymer | 0.20 |
| Potassium hydroxide | 0.20 |
| Purified water | Remaining part |

*a): Polyethylene glycol monostearate (n = 25) made by Tokyo Chemical Industry Co., Ltd.
*b): Monostearate glycerol made by Wako Pure Chemical Industries, Ltd.
*c) Risinolex made by Taiyo Corporation (Formulation Method)

Cetanol, scualane, stearic acid, γ-tocopherol, BHT, polyethylene glycol monostearate (25EO), the glycerin stearic acid monoester, and the glycerin ricinoleic acid monoester were mixed and dissolved by being heated to 70° C. (the resulting mixture was referred to as the antiseptic agent composition C (the product according to the present invention). On the other hand, EDTA-2Na, 1,3-butanediol, propylene glycol, carboxy vinyl polymer, potassium hydroxide, and purified water were mixed at room temperature (the resulting mixture was referred to as a mixture B). Then, the product according to the present invention and the mixture B were mixed and heated to 80° C., and were vigorously stirred, and thus a milky lotion was obtained.

(Compounding Property)

The product according to the present invention was immediately immingled with other components. Separation or precipitation was not found in the obtained milky lotion.

Since the antiseptic agent composition according to the present invention has an excellent antiseptic property against a wide range of bacteria, and also has an excellent compounding property, the antiseptic agent composition is suitably used as a component of an item to be antisepticized that is selected from food products, tableware, perfume cosmetics, cosmetics, external preparations for skin, oral hygiene products, quasi drugs, daily hygiene products, clothing, paints, and pet hygiene products.

What is claimed is:

1. An antiseptic agent composition comprising:
    a glycerin hydroxy fatty acid monoester at a concentration of 0.1 to 30 weight % that is an ester of glycerin and a hydroxy fatty acid having 8 to 18 carbon atoms; and
    an antiseptic agent that is a 1,2-octanediol at a concentration of 0.1 to 10 weight %,
wherein the glycerin hydroxy fatty acid monoester is glycerin ricinoleic acid monoester or glycerin caprylic acid monoester.

2. A method comprising compounding the antiseptic agent composition according to claim 1 with an item to be antisepticized that is selected from food products, tableware, perfume cosmetics, cosmetics, external preparations for skin, oral hygiene products, daily hygiene products, clothing, paints, and pet hygiene products so as to enhance an antiseptic property of the item to be antisepticized.

* * * * *